US008908828B2

(12) United States Patent
Burion et al.

(10) Patent No.: US 8,908,828 B2
(45) Date of Patent: Dec. 9, 2014

(54) CONTACT-FREE CONTROL OF MEDICAL IMAGING SYSTEMS

(75) Inventors: Steve Denis Burion, San Francisco, CA (US); Henry Hong Lin Liu, Fremont, CA (US)

(73) Assignee: Triple Ring Technologies, Inc., Newark, CA (US)

( * ) Notice: Subject to any disclaimer, the term of this patent is extended or adjusted under 35 U.S.C. 154(b) by 304 days.

(21) Appl. No.: 13/567,889

(22) Filed: Aug. 6, 2012

(65) Prior Publication Data

US 2014/0037068 A1 Feb. 6, 2014

(51) Int. Cl.
*G01N 23/04* (2006.01)

(52) U.S. Cl.
CPC .................................... *G01N 23/04* (2013.01)
USPC ............................................. 378/62; 700/65

(58) Field of Classification Search
CPC ........ A61B 6/541; A61B 6/504; A61B 6/481; G01N 23/04
USPC ............................ 378/62, 95; 700/17, 65, 83
See application file for complete search history.

(56) References Cited

U.S. PATENT DOCUMENTS 7,698,002 B2 * 4/2010 Music et al. .................... 700/17

* cited by examiner

*Primary Examiner* — Courtney Thomas
(74) *Attorney, Agent, or Firm* — Sabrina N. David; Joseph T. Lin

(57) ABSTRACT

The present invention pertains to a method and apparatus for contactless control of a medical imaging system. A medical image can be acquired and displayed, and an aspect of the image can be altered based on a tracked position of a user body part. The user can be sensed by a sensing device, and the user body part tracked by a tracking unit in a first processing unit. A second processing unit can be coupled to the first processing unit and can have a control unit for controlling the medical imaging system.

20 Claims, 4 Drawing Sheets

CONTACT-FREE CONTROL OF MEDICAL IMAGING SYSTEMS

FIELD OF THE INVENTION

The present invention pertains to the field of intraoperative medical imaging. The present invention also pertains to the field of human-computer interaction for medical imaging.

BACKGROUND

Interventional procedures can be a less invasive alternative to open surgeries for a growing number of applications. In an interventional procedure, a physician can insert a catheter or other implement into a patient through a relatively small incision and perform the procedure, whether it is insertion of a stent, removal of a malignant tissue, or any other manipulation, under image guidance. One type of image guidance is fluoroscopy, wherein real-time X-ray images are obtained by an X-ray tube and fluorescent screen or spatially resolved detector positioned on opposite sides of a patient. However, the dose of ionizing radiation delivered to patients during a fluoroscopy guided procedure, or other X-ray intensive imaging procedures, being somewhat of a concern, methods and apparatuses for dose-reduction have been developed.

A method and apparatus for adaptive exposure in X-ray imaging systems enable a surgeon to select a "region of interest" (ROI) within the available field of view of the X-ray imaging system, which can be imaged at a higher quality than the rest of the field of view. Adaptive exposure may be implemented in inverse geometry X-ray imaging systems wherein a plurality of discrete source locations, e.g. a scanning beam source or an array of discrete emitters, illuminate a spatially resolved detector in rapid sequence. The ROI may be exposed to a higher amount of X-ray flux to improve image contrast and quality relative to areas outside the ROI, so that these areas receive only the minimum amount of radiation necessary for the physician's analysis. ROI selection may be completed using a stylus or finger on a screen or otherwise tracing out an ROI on the presented X-ray image.

However, an operating room may be held to a high degree of sterility, requiring all objects to meet certain standards; a surgeon may be unable to touch a stylus or screen after beginning a procedure if the stylus or screen is not sterilized. What is needed is a method and apparatus by which a physician may control the ROI being implemented by an imaging system or other equipment parameters without risk of contamination or time-expensive processes during an interventional or other operating-room procedure. Embodiments of the present invention utilize an alternative means of human-computer interaction to offer a contact-free method and apparatus for ROI definition and related commands in an operating room.

SUMMARY

The present invention pertains to a method and apparatus for contactless control of a medical imaging system. A medical image can be acquired and displayed, and an aspect of the image can be altered based on a tracked position of a user body part, such as a hand or wrist. An additional body part can also be tracked and utilized in conjunction with the first body part to affect a second aspect of the image. A control zone can be defined a fixed distance from a body reference point, such as the chest, head, or point between the shoulders of the user, or in some other location. Image aspects may be the size or location of a region of interest.

The user can be sensed by a sensing device, and the user body part tracked by a tracking unit or units in a first processing unit. A second processing unit coupled to the first processing unit and can have a control unit for controlling the medical imaging system and can handle control zone definition. The medical imaging system may utilize a radiation source configured to deliver higher flux to a specified region of interest than to other regions in its field of view.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Figure 1:
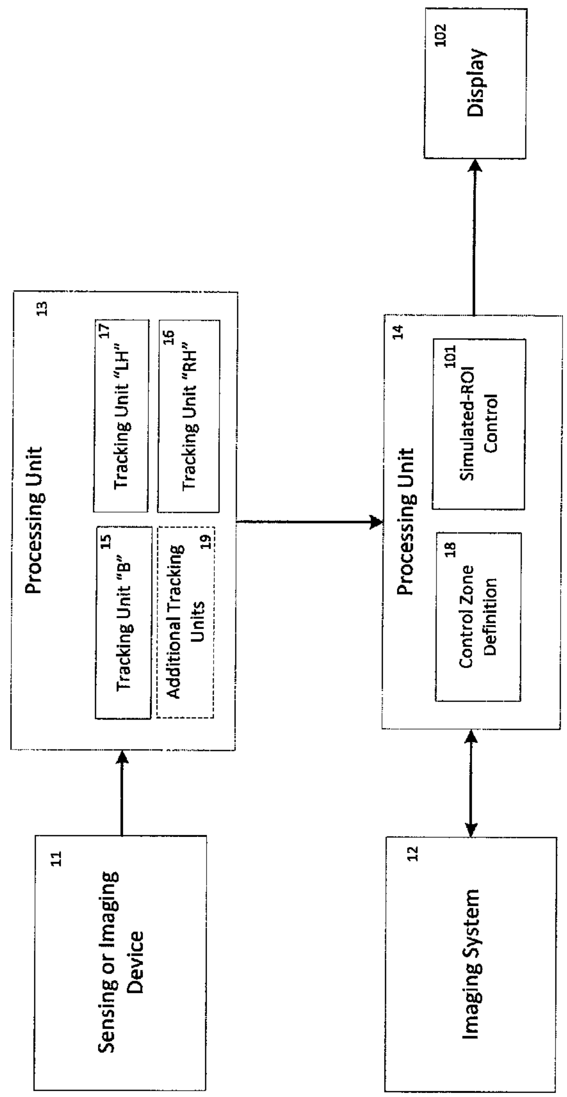
FIG. 1 is a diagram illustrating the components of one embodiment of the present invention.

FIG. 1 is a diagram illustrating the components of one embodiment of the present invention. In FIG. 1, arrows represent transmission of information. It can be seen that information from sensing device 11 can be transmitted to processing unit 13. Sensing device 11 may be a two-dimensional imaging device such as any type of digital camera or other digital imaging device. Alternatively, sensing device 11 may be a three-dimensional imaging device such as a set of two cameras providing stereoscopic information or may be a three-dimensional sensing device such as a system comprising a laser or lasers and a detector or detectors that can determine the distances and hence locations of all objects in its field of view. Sensing device 11 may also be some combination of the sensing and imaging devices just mentioned. Processing unit 13 may be a personal computer (PC), computer with Windows operating system, Macintosh, embedded processing unit, or other computer or processor. Processing unit 13 can comprise the functionalities of tracking unit "B" 15, tracking unit "RH" 16, tracking unit "LH" 17, and optionally additional tracking units 19. Processing unit 13 can also comprise a microprocessor, random access memory or hard disk drive.

Control zone definition 18 can refer to the delineation of a geometrically related set of coordinates fixed relative to the location of a human body, which can be provided by tracking unit "B" 15. If the coordinates of the right or left hand(s) or wrist(s), which can be provided by tracking unit "RH" 16 and tracking unit "LH" 17 respectively, coincide with coordinate (s) within the defined control zone, information passage to another processing block, simulated-ROI control 101, may be activated. Information passed to simulated-ROI control 101 may include the x-, y- and z-coordinates of one or both wrists of a tracked body, depending on whether one or both of the wrists entered the control zone.

In one embodiment of the present invention, simulated-ROI control 101 may be activated by the switch of a Boolean statement, such as "Hand Entered Control Zone," from "false" to "true." The status of such a Boolean statement may be checked for each set of image or sensed data, e.g. each frame, received from sensing device 11 by processing unit 13 through evaluation of the position(s) of relevant tracked body part(s) with respect to boundaries determined by control zone definition 18. The status of such a Boolean statement for a given frame may be stored and accessed during the processing of the subsequent frame such that a switch from "false" to "true" can be recognized and activate simulated-ROI control 101 while a continuation, such as "true" to "true," may not interfere with simulated-ROI control 101 if already running in processing unit 14. Similarly, a change from "true" to "false" may deactivate simulated-ROI control 101, and a continuation such as "false" to "false" may not initiate communication with simulated-ROI control 101.

In an embodiment of the present invention, Boolean statements may be evaluated as described for the positions returned by both tracking unit "RH" 16 and tracking unit "LH" 17. In this embodiment, the specific task carried out by simulated-ROI control 101 of processing unit 14 may be dependent on whether one or both statements are "true."

In some embodiments of the present invention, simulated-ROI control 101 may be activated without control zone definition 18. In these embodiments of the present invention, processing unit 13 may or may not be utilized prior to activation of simulated-ROI control 101. In one embodiment, positions of tracked body parts provided by processing unit 13 can be monitored for the occurrence of an activation event unrelated to a control zone, such as the tracing of a certain pattern, amount of time spent stationary, orientation with respect to one another, or any other discernible event. A single tracking unit or multiple tracking units may provide locations from which this type of activation event can be detected, and one-dimensional, two-dimensional, or three-dimensional locations may suffice.

In another embodiment of the present invention, control zone definition 18 may be replaced by any other type of switch, including but not limited to a foot pedal, voice command, button, or any other switch or cue, that can turn on simulated-ROI control 101. In this embodiment of the present invention, processing unit 13 may be activated along with simulated-ROI control 101.

Processing unit 14 may both receive information from and transmit information to imaging system 12. Imaging system 12 can be an X-ray imaging system, e.g. a fluoroscopic X-ray imaging system, or any other electromagnetic radiation-based imaging system, possibly capable of providing real-time video. Imaging system 12 may also represent any imaging or other medical device operated under sterile conditions, or where hands-free control may be useful.

Imaging system 12 may be a digital X-ray imaging system or other imaging system enabled to provide variable levels of X-ray radiation to regions of the patient within its field of view according to selection(s) by a surgeon or operator. Region(s) within the field of view that a surgeon or physician selects for higher fidelity, possibly higher exposure, imaging may be referred to as "region(s) of interest" or "ROI(s)." X-ray imaging system 12 may transmit image data to processing unit 14, which may display acquired X-ray images on display 102. X-ray imaging system 12 may also transmit information containing the current levels of X-ray radiation being delivered to regions within the field of view such that currently implemented ROI(s) can be demarcated on display 102.

Processing unit 14 may contain the functionality of simulated-ROI control 101 such that if it is receiving information from both processing unit 13 and X-ray imaging system 12, the movement of coordinates determined by tracking unit "RH" 16 and tracking unit "LH" 17, e.g. the coordinates of a body's right and left wrists or hands, may be used to alter the ROI demarcation(s) on display 102. If the user approves the alterations, information may be transmitted to X-ray imaging system 12, which can alter exposure levels accordingly.

Processing unit 14 may be a PC, computer with Windows operating system, Macintosh, embedded processing unit, or other computer or processor comprising the functionalities of control zone definition 18 and simulated-ROI control 101. Processing unit 13 and processing unit 14 may comprise two individual processors, a single processor, or more than two processors. Any number of processors or computers may be used to implement the functionalities (or processing blocks) of processing unit 13 and processing unit 14, e.g. tracking, control zone definition, and ROI control. It may also be noted that some processing may take place within other components of FIG. 1, e.g. image reconstruction within X-ray imaging system 12 or background subtraction, human body extraction, and tracking within sensing device 11.

Depending on the data available from a selected sensing device 11, tracking units may either be implemented in hardware or implemented through tracking software. Proper tracking units can be implemented such that embodiments of the present invention can track the location(s) of a reference body point or body points, e.g. the center of the chest, the head, or the two shoulders, provided by tracking unit "B" 15 or by some combination of tracking units, the location(s) of the left and/or right hand(s) or wrist(s) provided by tracking unit "RH" 16 and/or tracking unit "LH" 17 respectively, and/or any other body parts.

Control zone definition 18 may comprise boundaries of a cube, cuboid, sphere, polyhedra, cone, or any other shape. The boundaries of a shape may be defined as a fixed distance from a central or reference body point, e.g. such that they can move with the tracked body, or in another manner. The nearest boundary or center of a shape may be fixed 1 to 6 inches, 6 to 12 inches, 12 to 18 inches, 18 to 24 inches, 24 to 30 inches, or 30 to 36 inches from a reference body point, or any integer or non-integer number of inches within the enumerated ranges. For example, the boundary may be fixed 12", 13", 14", 15", 16", 17", 18", 19", 20", 21", 22", 23", 24", 25", 26", 27", 28", 29", or 30" from a reference body point, or any non-integer number of inches between the enumerated values. Such a central body point to which a control zone can be referenced may be a body point provided by tracking unit "B" 15, such as the chest of the tracked body. Alternatively, it may be an average of multiple body points provided by additional tracking units 19. In one embodiment of the present invention, the central body point to which the control zone is referenced is the average or some other composite of the positions of a tracked body's left shoulder, right shoulder, and chest. Since small, false variations in tracked locations, stemming from noise or otherwise unrelated to true motion, may exist, the position of a control zone related to an averaged or composite reference body point may be less prone to jitter compared to the position of a control zone related to a single, tracked body point.

Figure 2:
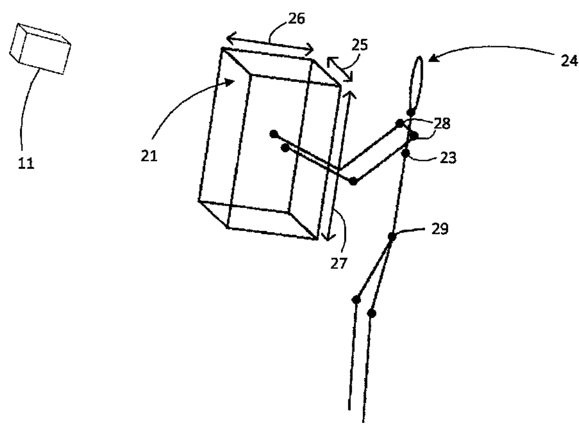
FIG. 2 is a diagram showing an exemplary control zone of one embodiment of the present invention.

FIG. 2 is a diagram showing an exemplary control zone of one embodiment of the present invention. It can be seen that control zone 21 can be defined such that it is a fixed distance from reference body point 23 of tracked body 24. While reference body point 23 may appear in FIG. 2 to be located on or near the chest of tracked body 24, reference body point 23 may be a single tracked location or an average or composite of surrounding body locations. In one embodiment of the present invention, control zone 21 can be referenced to reference body point 23 but remain parallel or otherwise oriented with respect to the imaging or sensing device 11. For example, tracked body 24 and control zone 21 as shown in FIG. 2 may have been generated by a user standing directly in front of imaging or sensing device 11 or may have been generated by a user standing at some angle relative to imaging or sensing device 11.

Referencing control zone 21 to reference body point 23 and orienting it relative to sensing device 11 is one method of generating a conveniently-positioned control zone with flexibility in system positioning with respect to the user. This feature may be particularly useful if sensing device 11 cannot be positioned directly in front of the surgeon during a procedure due to spatial requirements of other equipment, if the surgeon may need to access the control zone from various laterally spaced locations during the procedure, or for a variety of other reasons. However, any combination of position references and orientations for the control zone may be used. For example, control zone 21 may be referenced to a fixed location in space including but not limited to an operating table, piece of equipment, display 102, or other predetermined point in space. A stationary control zone may be particularly useful if a surgeon may be placing his or her hands through most of the nearby accessible space during the procedure and therefore prefers to turn toward or step to a different location to access the control zone. Another alternative may be for the control zone orientation to follow the orientation of the tracked body, the orientation of the tracked body possibly being defined by the positions of the body's chest and shoulders.

The dimensions of a control zone may be selected by the user or automatically determined. The dimensions of control zone 21, e.g. length 25, width 26, and height 27 of control zone 21, may be predetermined or may be determined by the system based on body tracking parameters. A predetermined value of height 27 or length 25 may be between zero and 8 feet, or any other value, as the field of view of sensing device 11 allows. For example, height 27 may be 6 to 12 inches, 12 to 18 inches, 18 to 24 inches, 24 to 30 inches, 30 to 36 inches, 36 to 42 inches, 42 to 48 inches, 48 to 54 inches, or 54 to 60 inches, inclusive, or any integer or non-integer number of inches within the enumerated ranges. Height 27 may further be 18", 19", 20" 21", 22", 23", 24", 25", 26", 27", 28", 29", 30", 31", 32", 33", 34", 35", or 36", or any non-integer number of integers between the enumerated values. Alternatively, height 27 and length 25 may extend across the entire available view of sensing device 11. A predetermined value of width 26 may be between zero and 4 feet, or any other value. For example, width 26 may be zero to 3 inches, 3 to 6 inches, 6 to 12 inches, 12 to 15 inches, 15 to 18 inches, 18 to 21 inches, 21 to 24 inches, 24 to 27 inches, 37 to 30 inches, 30 to 33 inches, 33 to 36 inches, 36 to 39 inches, 39 to 42 inches, 42 to 25 inches, or 45 to 48 inches, inclusive, or any integer or non-integer number of inches within the enumerate ranges. Width 26 may further be 4", 5", 6", 7", 8", 9", 10", 11", 12", 13", 14", 15", 16", 17", 18", 19" 20", 21", 22", 23" or 24", or any non-integer number of inches between the enumerated values. Alternatively, width 26 may extend from the side of the control zone nearest the user to the area nearest sensing device 11 within its field of view.

As an alternative to predetermined control zone dimensions, the system may include further tracking units so that the dimensions of control zone 21 can be referenced to certain body features; height 27 may extend from the top of shoulders 28 to hips 29 of the tracked body, and length 25 may extend outwards some fixed distance from the outside of shoulders 28. The locations of shoulders 28, hips 29, and any locations used to determine body metrics may be provided by additional tracking units 19. Any other parameters of a tracked body may be used to define the dimensions of a control zone.

In one embodiment of the present invention, control zone definition 18 can comprise creating a control zone by defining eight points that can serve as eight corners of a control zone, e.g. rectangular control zone 21. In sets of three or four, the eight points can then be used to define planes that serve as the outer boundaries of the control zone. Alternatively, fewer than eight or more than eight points can be defined and a control zone delineated by planes including at least three of the defined points. If a three-dimensional control zone is desired, the number of defined points may be four, five, six, seven, eight, nine, ten, eleven, twelve, or more.

Since any shape, e.g. a cube, cuboid, sphere, polyhedra, cone, or any other shape, may be used for the control zone, control zone definition 18 can comprise any one of a number of methods of control zone construction. For example, if a spherical control zone is desired, preliminary definition of a center point and a radius may be preferable to construction via corner points and planes.

Figure 3:
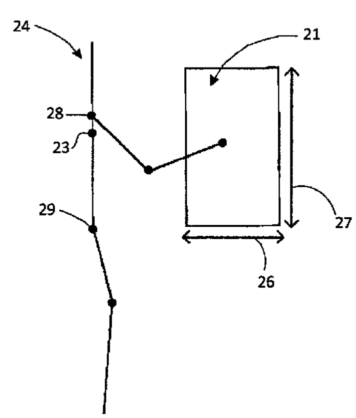
FIG. 3 is a diagram of a direct side view of a tracked body and control zone of one embodiment of the present invention.
Figure 4:
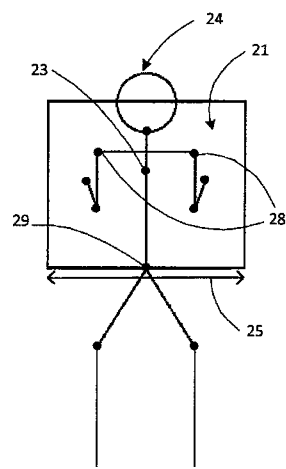
FIG. 4 is a diagram of a direct frontal view of a tracked body and control zone of one embodiment of the present invention.

An image or video of a simplified, e.g. stick, figure and a control zone may be provided on display 102. The figure may be relatively complete if processing unit 13 includes a sufficient number of additional tracking units 19 to construct a full stick-figure of the tracked body, e.g. a head, shoulders, elbows, knees, and so forth. Alternatively, display 102 may display only the locations provided by tracking unit "RH" 16, tracking unit "LH" 17, and/or tracking unit "B" 15, e.g. the location of the right hand or wrist, left hand or wrist, and/or reference body point, along with the control zone. Display 102 may display one, two, or more than two perspectives of tracked body locations and the control zone. One perspective may be a direct side view, as in FIG. 3, to provide the user with a clear indication of the distance between his or her hands or wrists and a defined control zone. Another perspective may be a direct frontal view, as in FIG. 4, so that the user can view the x- and y-coordinate motion of tracked body parts as seen by the sensing device 11. Other perspectives, in addition to or instead of direct side and frontal views, may be provided, including but not limited to views from 25, 30, 35, 40, 45, 50, 55, 60, 65, or 70 degrees, or some number of degrees between the enumerated values, above or below a direct frontal view, clockwise or counterclockwise from a direct side view, or some combination thereof.

Other visual cues or indications may be incorporated into views provided on display 102. Control zone 21 may be outlined or shaded with a color, and this color may change according to whether a tracked body part(s) has entered the control zone. For example, the control zone may be outlined or shaded in one color, e.g. green, when no relevant body parts are inside of the control zone, in a second color, e.g. yellow, when one tracked hand or wrist is inside of the control zone, and in a third color, e.g. red, when both tracked hands or wrists are inside of the control zone. Such visual cues or indications may aid the user in realizing when he or she has entered the control zone and activated simulated-ROI control 101. The first, second, and third colors may be any color including but not limited to green, red, yellow, purple, blue, orange, white, or black.

Control zone definition 18 may be included in embodiments of the present invention in which sensing device 11 is capable of sensing or imaging three dimensions; two dimensions may be used for simulated-ROI manipulation and a third primarily for activation and deactivation of simulated-ROI control 101(via identification of control zone entrance and exit). In embodiments of the present invention in which sensing device 11 images or senses two dimensions, activation and deactivation of simulated-ROI control 101 may be accomplished by voice command, a foot pedal, or any other method. Such a trigger may be incorporated in three-dimensional systems as well. It may serve as a replacement for control zone definition 18 or as a preliminary step which can turn control zone 21 on and off as specified by the user. It may be desirable for the control zone 21 to be turned on and off during a procedure so that simulated-ROI control 101 cannot be accidentally activated by a surgeon's motions near or in the control zone.

Figure 5:
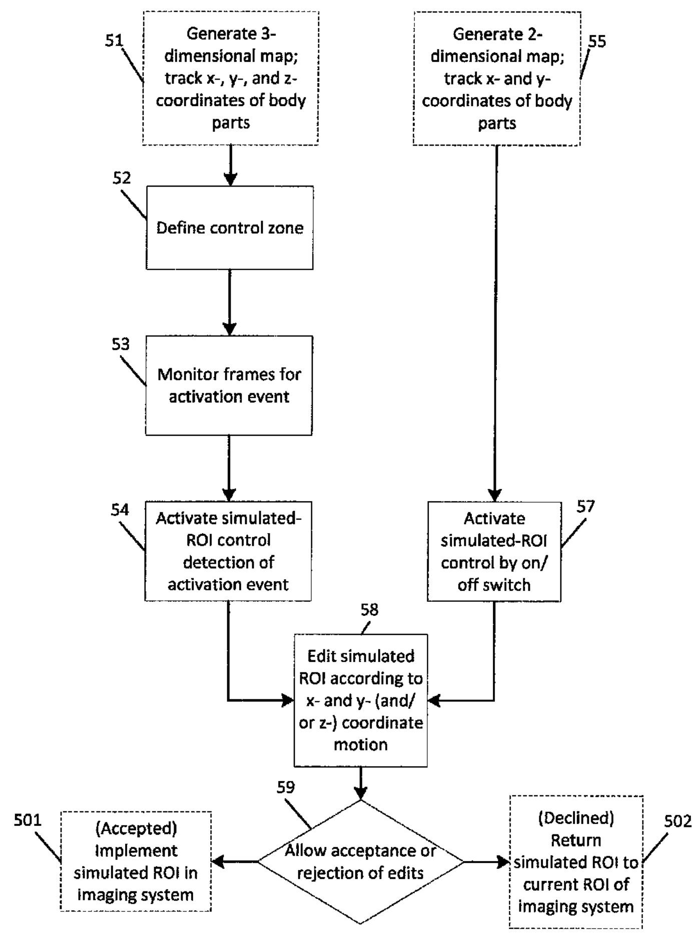
FIG. 5 is a flow diagram showing steps of one embodiment of the present invention that can utilize two-dimensional or three-dimensional sensing or imaging devices.

FIG. 5 is a flow diagram showing steps of one embodiment of the present invention that can utilize two-dimensional or three-dimensional sensing or imaging devices. Dashed lines around step 51, step 55, step 501, and step 502 indicate that these steps can be completed by other systems, e.g. sensing device 11 and X-ray imaging system 12.

As previously discussed, the first step for a system utilizing a three-dimensional sensing or imaging system once relevant body locations have been obtained, may be step 52, defining a control zone. Once this control zone is defined, the x-, y-, and z-coordinates of tracked body parts relative to the defined control zone may be monitored (step 53) such that simulated-ROI control 101 is activated upon detection of activation event, e.g. when one or both hands or wrists enter the control zone, as in step 54. For example, the dimensions of simulated ROI 21 may be defined by geometric "if/then" statements relating the positions of tracked body parts to positions at which simulated-ROI control 101 may be activated.

In the embodiment of FIG. 1, simulated-ROI control 101 may be executed in processing unit 14 and assisted by display 102. A possible connection between processing unit 14 and X-ray imaging system 12 is further detailed in step 58, step 59, step 501, and step 502 of FIG. 5. A simulated ROI, e.g. an ROI displayed against an X-ray image background such as a pre-acquired sequence or video on display 102, can respond to user motions within the control zone, as opposed the ROI being executed by X-ray imaging system 12 responding to every user motion in the control zone. Displaying changes to a simulated rather than actual ROI may allow the user time to view and consider potential changes before having the changes implemented by the X-ray imaging system. The intermediate step of editing a simulated ROI may also reduce unnecessary exposure to areas of the patient outside the ROI that may stem from the user overly enlarging the ROI or moving it over an unintended region before reaching a correct ROI size and position. However, in some embodiments of the present invention, including those that may not utilize ionizing radiation for imaging, the ROI being executed by the system may be edited in real time. In the following description, "simulated ROI" may be understood to represent the actual ROI of the system for such embodiments.

Steps in FIG. 5 may occur while X-ray imaging system 12 is not actively acquiring images. During procedures, surgeons may turn X-ray acquisition on and off to avoid exposing the patient and medical personnel to X-ray radiation during stages of a procedure where X-ray guidance is not necessary. While acquisition is off, the screen or display of the X-ray imaging system which displays X-ray images or video may continuously display a previously acquired X-ray image loop. This previously acquired video loop may provide landmarks on which a simulated ROI can be drawn or edited and can be displayed on display 102. Alternatively, a single frame or short video loop acquired without any ROI being executed by the system, e.g. with the system imaging the entire field of view with equal exposure, may be a background over which a simulated ROI may be displayed. The latter, i.e. unfiltered, background may be useful if the user is likely to wish to enlarge or significantly move the ROI during the procedure, as all regions of the potential field of view (FOV) will be visible. The former, i.e. recently acquired, background may be desirable for other cases, e.g. if the surgeon is likely to shrink or make small changes to the ROI during the procedure, as editing can be based on the most current images available.

A simulated ROI may be displayed in a variety of ways. A colored, e.g. green, red, yellow, purple, blue, orange, white, or black, outline may be drawn around the simulated ROI. An ROI shape may have been selected by the user prior to activating simulated-ROI control 101 or otherwise editing the simulated ROI, such that this colored outline can be a circle, square, rectangular, trapezoidal, polygonal, triangular, or any other preselected shape. The shape and size of the simulated ROI may respond to user motions within the control zone. An option may also exist for additional or alternative simulated ROI(s) of different shape(s) than the originally selected simulated ROI to be made available to the user once the procedure has begun. This option may be beneficial as a user may wish to use an ROI of a different shape once a catheter or other implement has been inserted into a patient.

Figure 6:
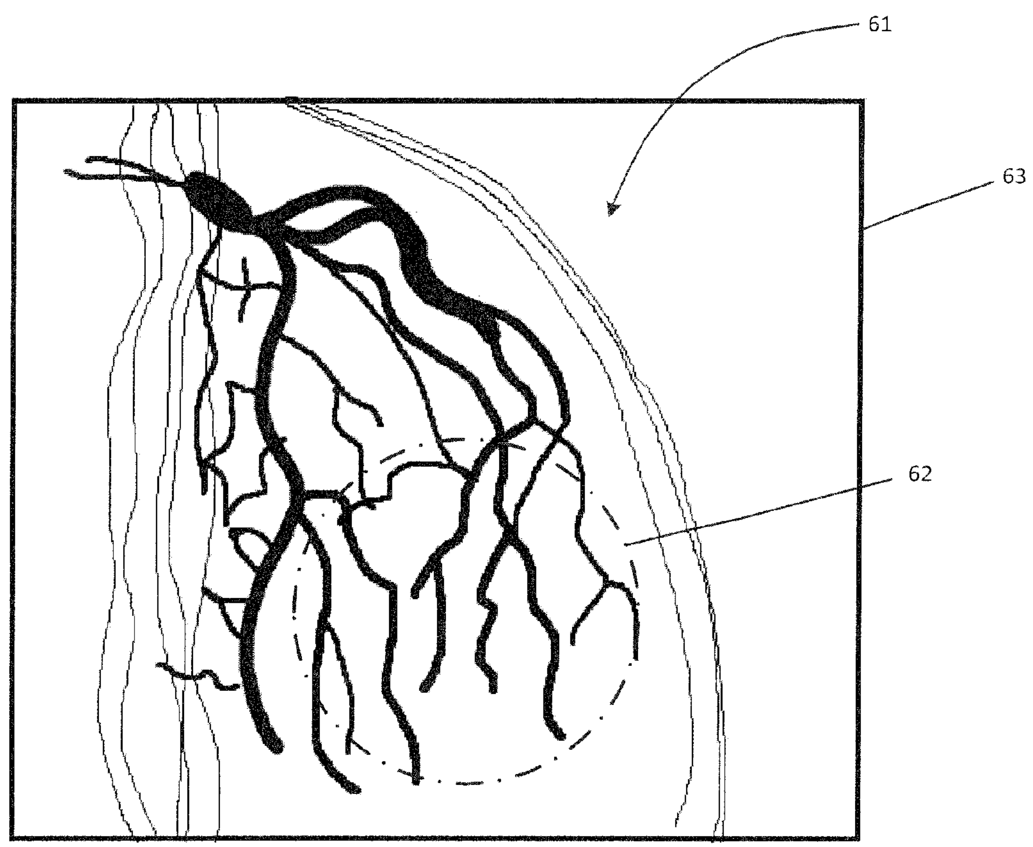
FIG. 6 is a diagram of one example of a possible simulated ROI appearance of one embodiment of the present invention.

FIG. 6 is a diagram of one example of a possible simulated ROI appearance of one embodiment of the present invention. In FIG. 6, the preselected ROI shape is a circle. Background 61 within frame 63 represents a grayscale X-ray image of the cardiac region of a patient. Simulated circular ROI 62 has been positioned such that it encompasses a specific region of the heart and not an extraneous amount of surrounding tissue or other regions of the heart. The outline of simulated circular ROI 62 (and any ROI outlines) may be green, red, yellow, purple, blue, orange, white, or black, or any other color with good contrast against displayed image backgrounds, e.g. a grayscale X-ray image background. In FIG. 6, simulated circular ROI 62 is represented with a dashed line, though in embodiments of the present invention it may be represented with a solid line, dashed line, dotted line, or any other type of demarcation.

Step 58 may include the implementation of scaling or other transformations between tracked movements and changes to the simulated ROI. The correlation between the magnitude of user motions and the magnitude of changes to the simulated ROI may depend on the distance between the user and the imaging device as greater distance may cause the motions to appear relatively smaller. If a sensing, e.g. laser and camera, device is utilized, the actual distance between the tracked body and the device may be obtained and accounted for in a correlation method. It may also be desirable to allow the correlation to be tunable or adjustable, as variations may exist in user preference regarding the optimal relationship between hand motion and resultant ROI change(s).

Predetermined "user motion to ROI change" ratios may include but not be limited to 5:1, 4:1, 3:1, 2:1, 1:1, 1:2, 1:3, 1:4, and 1:5 or any ratios between the enumerated values. Ratios may also include non-integer components such as 3.5:1, 3.25:1, 2.75:1, 2.5:1, 2.25:1, 1.75:1, 1.5:1, 1.25:1, and the reverse of all such ratios. However, ratios may be highly dependent on the geometry of the system and carry any other values, including above or below 5:1 or 1:5.

Once simulated-ROI control 101 has been enabled simulated ROI editing may depend only on the changes in x- and y-coordinates of tracked body parts between frames. Z-coordinates, if available, may be monitored for the purpose of turning off simulated-ROI control 101. Alternatively, available z-coordinates may be incorporated into simulated ROI editing.

Changes in the size of a simulated ROI in step 58 may depend on the change in the relative distance between a tracked left hand or wrist and a tracked right hand or wrist corresponding to a given tracked body in the view of sensing device 11. The relative distance between the two tracked hands or wrists may be computed for each frame such that changes in the relative distance can be computed on a frame-by-frame basis by subtracting the relative distance in the present frame from the relative distance in the previously acquired frame. The relative distance may computed as $d_{rel}=\sqrt{(x_{right}-x_{left})^2+(y_{right}-y_{left})^2}$ where $x_{right}$ and $x_{left}$ are the x-coordinates of the right and left hands or wrists respectively and $y_{right}$ and $y_{left}$ are the y-coordinates of the right and left hands or wrists respectively. The difference between relative distances in contiguous frames, $\Delta d_{rel}$, may be scaled by some factor. Changes to the dimensions of a simulated ROI between frames, possibly shown on display 102, may be based on the absolute or scaled value of $\Delta d_{rel}$ between frames from sensing device 11.

Changes to the location of a simulated ROI in step 58 may be based on user motion and similarly computed, though a vector, e.g. magnitude with direction, rather than scalar, e.g. magnitude only, quantity may be computed by treating x-coordinate changes and y-coordinate changes independently. For example, the change in the x-coordinate of a single hand or wrist, $\Delta x=x_{f1}-x_{f2}$, (where f1 and f2 indicate the immediately previous frame and the present frame respectively) may be scaled by a factor and may be used to change the x-coordinate of the center of the simulated ROI by the absolute or scaled value. The change in the y-coordinate of the single hand or wrist may be analogously and simultaneously computed and implemented.

Though the methods above are described in terms of the variables x and y, any two coordinates can be utilized in embodiments of the present invention, including but not limited to x and y, x and z, or y and z. Axes may be defined such that the y-axis is vertical in the field of view of the imaging or sensing device, e.g. parallel to a head-to-foot line of a standing tracked body, x-axis is horizontal in the field of view of the imaging or sensing device, e.g. parallel to a shoulder-to-shoulder line of a standing tracked body, and z-axis traverses near-to-far in the field of view of the image of sensing device. However, axes may also be defined in any other manner.

Embodiments of the present invention may edit a simulated ROI according to relative changes in position(s) between frames, e.g. by following methods just described. In embodiments of the present invention using relative changes, the entrance of a tracked body part into the control zone may not immediately edit the simulated ROI. For example, the position of the simulated ROI may not change to a new location based on where in the control zone a tracked hand or wrist entered but may instead remain stationary until the tracked hand or wrist moves in the x- or y-direction relative to the coordinates of its entrance; motion of the simulated ROI may be relative to the entrance point of the tracked hand or wrist. This feature may contribute to easy and intuitive use of embodiments of the present invention.

Alternatively, the coordinates of tracked body parts within the control zone in a given frame, as opposed to relative changes in coordinates between frames, may be utilized to compute the positioning or size of a simulated ROI in X-ray image space. In embodiments of the present invention using the coordinates of tracked body parts in this manner, the x- and y-dimensions of the control zone may be proportional to the x- and y-dimensions of the X-ray image or images shown on display 102 and may be related to the dimensions of the X-ray image or images by a scale factor. A scale factor relating the dimensions of a control zone to the dimensions of image(s) on display 102 may be applied to the x- and y-coordinates of a tracked body part within the control zone in order to determine the image plane coordinates over which the simulated ROI should be positioned. If two tracked hands or wrists are detected in the control zone, the x- and y-coordinates of the hands or wrists may be similarly identified and scaled to determine the outer edges of the simulated ROI in X-ray image display 102. Embodiments utilizing actual coordinates within the control zone may enable an accustomed user to position and resize a simulated ROI more quickly than with embodiments of the present invention utilizing relative changes.

In one embodiment of the present invention, simulated-ROI control 101 may be activated only by the detection of tracked body parts, e.g. hands or wrists, being held stationary within the control zone for a given amount of time, e.g. ⅓ of a second, ½ of a second, ¾ of a second, 1 second, 2 seconds, 3 seconds, or 4 seconds, or a non-integer number of seconds between the enumerated values. If an if/then statement, or any similar mechanism, is used in step 53 to relate locations of tracked body parts with the control zone and activate simulated-ROI control 101, the condition may involve a set number of frames or given amount of time passing wherein the motion of tracked hands or wrists within the control zone is below some threshold value. The number of frames or length of time which must pass for simulated-ROI control 101 to be activated may be fixed or may be a user option. A benefit of delaying activation of simulated-ROI control 101 may be a decrease in the likelihood of simulated-ROI control 101 being unintentionally activated; it may be likely that a user passes hands or wrists through the control zone while performing aspects of the surgical procedure, and it may be less likely that the user holds them stationary within the control zone apart from when intentionally activating simulated-ROI control 101.

A similar mechanism may be implemented for deactivation of simulated-ROI control 101. After activation, simulated-ROI control 101 may be deactivated if a deactivation event is detected e.g. tracked hands or wrists remaining stationary within the control zone for a fixed amount of time. The fixed amount of time resulting in deactivation may be equal to the amount of time used for activation, or may be more or less than this amount. For example, the fixed amount of time may be one ⅓ of a second, ½ of a second, ¾ of a second, 1 second, 2 seconds, 3 seconds, or 4 seconds, a non-integer number of second between the enumerated values, or any other length of time. An if/then statement, or other mechanism, governing simulated-ROI control 101 deactivation may depend on relative motion remaining below a threshold value for a given number of frames or amount of time. Embodiments of the present invention wherein control zone exit is the sole mechanism for deactivation of simulated-ROI control 101 may require the relative x- and y-positions of tracked hands or wrists to be maintained while withdrawing from the control zone in the z-direction in order to maintain simulation of a desired ROI size or location. The option of deactivating the control zone by holding hands or wrists stationary within the control zone may be desirable for a user concerned about maintaining simulation of an exact ROI size or location.

The parallel system paths of FIG. 5 meet at step 58, though the preceding steps may differ slightly. If only x- and y-coordinates are tracked, simulated-ROI editing of step 58 may be enabled by some sort of switch in step 57, e.g. a voice-activated switch or physical button.

In step 59 an embodiment of the present invention may allow the user to decide whether or not the changes made to a simulated ROI in step 58 should be implemented in the next phase of X-ray image acquisition. If changes made in step 58 are accepted, information sufficient to implement the simulated ROI may be sent to X-ray imaging system 12. When changes are accepted, information may be passed from processing unit 14 to X-ray imaging system 12 as shown in FIG. 1. If changes made in step 58 are rejected, information sufficient to simulate the last ROI implemented by X-ray imaging system 12 may be used to undo all changes made in step 58. When changes are rejected, information may be passed from X-ray imaging system 12 to processing unit 14 as shown in FIG. 1. Any method for the user to accept or reject changes may be used, including but not limited to voice commands; voice-recognition; physical devices, e.g. a button, pedal, or mouse; or additional virtual features. Additional contact-free methods of accepted or rejecting changes may be recognition of specific user motions, such as the tracing of a predetermined shape or other sign; definition of additional control zones that can serve as accept/reject buttons; or any other method utilizing sensing or imaging device 12 and available tracking units.

If simulated-ROI changes are rejected, but tracked body parts are still detected within the control zone and motion-tracking has not been otherwise switched off, the simulated ROI may be reset to match the ROI currently implemented by the X-ray imaging system. If no ROI is currently being implemented by the imaging system, the simulated ROI may be removed and re-defined by subsequently detected motions. Embodiments of the present invention may allow a user to either begin to edit the simulated ROI again or switch off simulated-ROI control 101 by withdrawing from the control zone or by another method.

If changes to the simulated ROI are accepted, they may be passed to X-ray imaging system 12. X-ray imaging system 12 may be capable of selectively exposing areas of the patient by electronic collimation, mechanical collimation, or some other mechanism, and may implement the selected ROI accordingly.

An X-ray imaging system may be capable of providing varied exposure according to more than one defined ROI. Features may be incorporated in embodiments of the present invention that allow users to manipulate more than one ROI. In one embodiment, additional control zones may be defined and displayed on display 102. These additional control zones may be smaller than the previously discussed, primary control zone and essentially serve as switches determining which one of multiple ROI's will be controlled if the user enters the primary control zone. For example, if two ROI's are being implemented by X-ray imaging system 12, two secondary control zones may be defined and displayed. The secondary control zones may be referenced to the same body point or other point as the primary control zone and positioned in space outside of the primary control zone, for example to the left or right of the user if the primary control zone is in front of the user. The system may detect the "touching" of the secondary control zones and select a specific simulated ROI corresponding to that secondary control zone for editing. The correlation between secondary control zones and simulated ROI's may be indicated on display 102 using color, e.g. matching the color of the outline of a simulated ROI to the shading of a secondary control zone, or by any other methods. Detection of a second "touching" of the secondary control zone may trigger deactivation of simulated ROI control for the corresponding simulated ROI.

More than two ROI's may be implemented by X-ray imaging system 12, and more than two secondary control zones may be defined. Alternatively, other configurations may be used to select one of multiple ROI's. A single secondary control zone may be created, and it may switch control from one simulated ROI to another simulated ROI according to a predetermined sequence when a "touch" is detected, using color on display 102 or some other method to indicate which simulated ROI is controlled following subsequent "touches" of or motion within the secondary control zone.

A secondary control zone or secondary control zones may also be provided for the user to select a shape for the simulated ROI, as previously discussed. A number of secondary control zones may be equal to the number of available shapes such that each secondary control zone may be associated with a given shape, or a there may be a single secondary control zone that can switch the currently simulated ROI to the next shape in a sequence of available simulated ROI shapes when a "touch" is detected.

In one embodiment of the present invention, an embodiment of the present invention may register user motion as a "touch" by utilizing Boolean statements similar to those previously discussed for the primary control zone, e.g. "Hand Entered Control Zone" and "Hand Left Control Zone." However, directions sent to processing unit 13 may depend on slightly more complex combinations of these statements. For example, an occurrence, e.g. a switch from "false" to "true," of a statement such as "Hand Touched Control Zone" may actually be a combination of multiple statements such as "Hand Entered Control Zone," "Hand Remained in Control Zone for X Milliseconds," and "Hand Left Control Zone." "Hand Touched Control Zone" being "true" may direct processing unit 13 to control a specific simulated ROI. The "X" in "Hand Remained in Control Zone for X Milliseconds" can denote some number of milliseconds, seconds, or other unit of time, for which a tracked hand or wrist remaining in the control zone can initiate a "touch" being recorded. This number of millisecond may be 0 to 10 milliseconds, 10 to 20 milliseconds, 20 to 30 milliseconds, 30 to 40 milliseconds, 40 to 50 milliseconds, 50 to 60 milliseconds, 60 to 70 milliseconds, 70 to 80 milliseconds, 80 to 90 milliseconds, 90 to 100 milliseconds, or any other number of milliseconds within the enumerated ranges, or above. While a statement such as "Hand Touched Control Zone" is true, a similar combination of statements, e.g. "Hand Entered Control Zone," "Hand Remained in Control Zone for X Milliseconds, and "Hand Left Control Zone," may switch the statement such as "Hand Touched Control Zone" back to "false" and deselect the given simulated ROI. Any other combination of statements, events, or other means may be used to enable selection of a specific simulated ROI for control by processing unit 13 in a hands-free manner.

Alternatively, a foot pedal, voice command, or other physical mechanism may be used to switch the currently displayed simulated ROI to the next shape in a sequence of available shapes. Contact-free methods such as recognition of specific user motions, e.g. the tracing of a predetermined shape or other sign; definition of additional control zones that can serve as accept/reject buttons; or any other method utilizing sensing or imaging device 12 and available tracking units may also be utilized.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method of contactless control of a medical imaging system comprising:

acquiring a medical image from said medical imaging system;

displaying said medical image;

tracking a first position of a first body part of a user; and altering a first aspect of the medical image based on said first position.

2. The method of contactless control of a medical imaging system of claim 1 further comprising:

determining an altered acquisition parameter for said medical imaging system based on alteration of said first aspect; and implementing said altered acquisition parameter in said medical imaging system.

3. The method of contactless control of a medical imaging system of claim 1 further comprising defining a control zone.

4. The method of contactless control of a medical imaging system of claim 3 further comprising:

selecting a body reference point on said user;

tracking said body reference point; and positioning said control zone a fixed distance from said body reference point.

5. The method of contactless control of a medical imaging system of claim 4 wherein said body reference point is chest of said user.

6. The method of contactless control of a medical imaging system of claim 4 wherein said body reference point is head of said user.

7. The method of contactless control of a medical imaging system of claim 4 wherein said body reference point is a midpoint between two shoulders of said user.

8. The method of contactless control of a medical imaging system of claim 1 wherein said first body part is a hand of said user.

9. The method of contactless control of a medical imaging system of claim 1 wherein said first body part is a wrist of said user.

10. The method of contactless control of a medical imaging system of claim 1 wherein said first aspect is a location of a region of interest in said medical image.

11. The method of contactless control of a medical imaging system of claim 1 further comprising:

defining a control zone;

establishing a set of image options for said medical image;

monitoring said first position with respect to said control zone; and switching between image options of said set if said first position touches said control zone.

12. The method of contactless control of a medical imaging system of claim 11 wherein said image options are shapes for a region of interest in said medical image.

13. The method of contactless control of a medical imaging system of claim 1 further comprising:

tracking a second position of a second body part of said user; and altering a second aspect of the medical image based on said first position and said second position.

14. The method of contactless control of a medical imaging system of claim 13 wherein said second aspect is a size of a region of interest in said medical image.

15. A contactless control system for medical imaging comprising:

a sensing device configured to sense a user;

a first processing unit coupled to said sensing device;

a tracking unit in said first processing unit for determining a first position of a first body part of said user;

a second processing unit coupled to said first processing unit;

a medical imaging system coupled to said second processing unit;

a display coupled to said medical imaging system for displaying a medical image; and a control unit in said second processing unit for controlling said medical imaging system.

16. The contactless control system of claim 15 further comprising a second tracking unit for determining a second position of a second body part of said user.

17. The contactless control system of claim 15 wherein said second processing unit is configured to define a control zone within a field of view of the sensing device.

18. The contactless control system of claim 17 further comprising a second display configured to show said first position and said control zone.

19. The contactless control system of claim 15 further comprising a second tracking unit configured to track a body reference point on said user.

20. The contactless control system of claim 15 wherein said medical imaging system comprises a radiation source configured to deliver higher radiation flux to a region of interest than to other regions.

* * * * *